United States Patent [19]

Twilley et al.

[11] Patent Number: 4,919,997

[45] Date of Patent: Apr. 24, 1990

[54] MELT-BLOWN WATER-ABSORBING TISSUES AND MATTS

[75] Inventors: Ian C. Twilley, Chester; Robert A. Lofquist, Richmond, both of Va.

[73] Assignee: Allied-Signal Inc., Morris Township, Morris County, N.J.

[21] Appl. No.: 117,790

[22] Filed: Nov. 6, 1987

[51] Int. Cl.[5] .................... B32B 17/00; D01G 3/00; D03D 3/00
[52] U.S. Cl. .................................. 428/227; 428/221; 428/300; 428/401; 428/903; 428/357
[58] Field of Search ............... 428/227, 230, 231, 288, 428/296, 232, 171, 172, 903, 394, 392, 395, 397, 357, 359, 360, 221, 401, 300

[56] References Cited

U.S. PATENT DOCUMENTS

| | | | |
|---|---|---|---|
| 3,369,057 | 2/1968 | Twilley | 260/857 |
| 3,594,266 | 7/1971 | Okazaki et al. | 428/395 |
| 3,654,370 | 4/1972 | Yeakey | 564/480 |
| 3,946,089 | 3/1976 | Furukawa et al. | 428/395 |
| 4,578,451 | 3/1986 | Weaver et al. | 528/292 |
| 4,724,184 | 2/1988 | Killian et al. | 428/227 |

OTHER PUBLICATIONS

Textile Research Journal, vol. 55, No. 6, Jun. 1985, pp. 325–333, "Hydrophilic Nylon for Improved Apparel Comfort".

*Primary Examiner*—Lorraine T. Kendell

[57] ABSTRACT

A melt-blown water-absorbing matt of fibers comprises a block copolyetheramide having polyether and polyamide segments. The matt structure provides excellent water absorbency and displays good resilience when exposed to humid conditions.

7 Claims, No Drawings

MELT-BLOWN WATER-ABSORBING TISSUES AND MATTS

BACKGROUND OF THE INVENTION

1. Field of the Invention

The invention relates to a melt-blown water-absorbing matt of organic fibers made primarily from a block copolyetheramide polymer having polyamide and polyether segments.

2. Description of Related Art

The block copolymer from which the melt-blown matts of the present invention are made have been used to form hydrophilic nylon fibers, as disclosed in the article "Hydrophilic Nylon for Improved Apparel Comfort" by R. A. Lofquist et al., published in Textile Research Journal Volume 55, no. 6, pages 325-333 June of 1985.

The addition of amine-ended polyethylene glycol to nylon 6 has been known. See U.S. Pat. No. 3,454,534 to Crovatt issued July 8, 1969, and U.S. Pat. No. 3,044,987 to Schaefgen et al. issued July 17, 1962. U.K. Patent 1,108,812 to Oldham published Apr. 3, 1968, discloses polyamide condensation products suitable for forming elastic shaped articles such as fibers. U.S. Pat. No. 4,622,263 to Ando et al. issued Nov. 11, 1986, discloses a melt-blown fiber web whose main component is a block copolyetherester having polyester and polyether segments in the molecule. The melt-blowing process for production of microdenier fibers of thermoplastic fiber forming material is generally known. See for example the article "Microdenier Fibers: A Progress Report" by Wayne P. Sorensen, published in Fiber Producer, February, 1984, pp 29–30.

SUMMARY OF THE INVENTION

The present invention comprises a melt-blown water-absorbing matt of fibers comprising a block copolyetheramide having a number average molecular weight of from about 10,000 to about 35,000 and having polymer segments of the following structure:

(A) a polyether segment consisting predominantly of

where c is at least 1, (a+c) is at least 1 but less than 10 and b is at least 10 but less than 150;

(B) a polyamide segment consisting of at least one of the following:

   (1)

   (2)

where $R_1$, $R_2$ and $R_3$ are each selected from the same or different alkylene or substituted alkylene moieties of from 4 to 11 carbons and difunctional aromatic moieties; wherein the concentration of segment A in the copolymer is between from about 10 to about 50 percent by weight of copolyether amide.

DESCRIPTION OF THE PREFERRED EMBODIMENT

The melt-blown water-absorbing matt of the present invention is formed from a block copolyetheramide having a number average molecular weight of from about 10,000 to about 35,000. The block copolyether amide contains polymer segments which are prepared by the amination of a polyether formed by treating a polyethylene glycol with an alkylene oxide having at least three carbon atoms, preferably propylene oxide.

The copolyether amide polymer segments have the following structure:

(A) a polyether segment consisting predominantly of

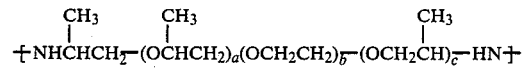

where c is at least 1, (a+c) is at least 1 but less than 10 and b is at least 10 but less than 150;

(B) a polyamide segment consisting of at least one of the following

   (1)

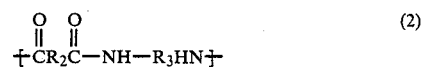   (2)

where $R_1$, $R_2$ and $R_3$ are each selected from the same or different alkylene or substituted alkylene moieties of from 4 to 11 carbons and difunctional aromatic moieties, wherein the concentration of segment A in the copolyether amide is from about 10 to about 50 percent by weight of copolyether amide. A phenolic antioxidant is preferably used in the copolyether amide where the ratio of antioxidant to polyether segment is greater than 0.01 but less than 0.1 by weight. By "predominantly" is meant 90 percent or more.

In order to achieve higher weight fractions of segment A, it is necessary to either have high molecular weight (b above about 25) segment A or to use carboxylic acid terminator for segment B. It is preferred to add a carboxylic acid as a terminator for the segment B, more preferably a dicarboxylic acid.

The commercial preparation (see U.S. Pat. No. 3,654,370, hereby incorporated by reference) of the above polyether diamine segment A when (a+c) is less than 10 also produces a polyether monoamine segment in amounts of up to 10 percent, typically 5 to 10 percent, by weight of the total polyether segment. This polyether monoamine segment is hydroxy terminated and has the following structure,

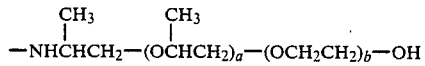

wherein a, (a+c), and b are all as defined above.

It is preferred that the total of a and c in segment A is from 3 to 4 and b is from 20 to 75, more preferably 40 to 50.

Preferably, the polyamide segment B has $R_1$ equal to $(CH_2)_5$.

The dicarboxylic acid is preferably selected from the group consisting of terephthalic, adipic, azelaic, isophthalic, dodecanedioic, sebacic and naphthalene dicarboxylic acid, most preferably the former.

The phenolic antioxidant is preferably selected from the group consisting of 4,4′-butylidenebis(6-tertiarybutyl-3-methylphenol); 4,4′-methylenebis-(6-t-butyl-o-cresol); 1,3,5-trimethyl-2,4,6-tris(3,5-di-t-butyl-4-hydroxybenzyl) benzene; tetrakis[methylene(3,5-di-t-butyl-4-hydroxy-hydrocinnamate)]methane; N,N′-hexamethylene bis(3,5-di-tert-butyl-4-hydroxyhydrocinnamamide); 1,3,5-tris(3,5-di-t-butyl-4-hydroxybenzyl)-s-triazine-2,4,6-(1H,3H,5H)-trione.

A preferred antioxidant is Irganox 1010, made by Ciba-Geigy, a tetrafunctional hindered phenolic antioxidant containing four ester groups per molecule, tetrakis[methylene-(3,5-di-t-butyl-4-hydroxy-hydrocinnamate)]methane.

An animated polyethylene glycol useful in the invention is an amine-ended derivative of polyethylene glycol known as Jeffamine ED2001 (hereafter polyether diamine or PED), commercially available from Texaco Chemical Company, PED, a white waxy solid with a melting point of about 45° C., is made by reacting one mole of polyethylene glycol of about 2000 molecular weight with three to four moles of propylene oxide in order to convert the terminal hydroxyls to secondary hydroxyls. From about 90 to 95 percent of these secondary hydroxyl are then converted to primary amines by a proprietary process (U.S. Pat. No. 3,654,370). A material made by that or a similar process is suitable for creating the polymer segments of the preferred block copolyether amides.

Poly(oxyethylene)diamines can also be made by treating polyethylene glycol with acrylonitrile, and then hydrogenating the product. Such materials have been made in Japan, but the process is apparently more expensive, and this material has not been readily available.

The length of the polyethylene glycol chain affects the moisture regain of the glycol and of the polymer of which it is a part. The long-chain polyether diamine used to create the polyether segment is preferably a polyethylene oxide diamine having a molecular weight in the range of 600 to 4000. When use is made of a polyethylene oxide diamine having a molecular weight of less than 600, the proportion thereof to be incorporated in the copolyether amide is prohibitively high. The most favorable results are obtained when the long-chain glycol is a polyethylene oxide glycol having a molecular weight in the range of 900 to 2500.

The manufacture of the melt-blown nonwoven structure of the present invention from copolyether amides may be carried out by known melt-blowing processes. Polymer pellets are melted in an extruder which feeds a melt-blowing dye. Hot high velocity air impinges on the polymer filaments emerging from the die capillaries and attenuates the fiber down to diameters of less than 10 microns. The attenuated fibers are blown onto a cylindrical screen and wound up in the form of a matt. The matt can be needle punched to increase matt integrity.

Fibers making up a melt-blown matt structure have a major influence on the absorbency characteristics, particularly rate of uptake and absorbent capacity. The polymer type, whether hydrophobic or hydrophilic, used to make the fiber influences the inherent absorbency of the resultant nonwoven structure. A hydrophilic fiber can absorb water via fiber inbibition as well as by holding water in the pores of the matt structure. A hydrophobic fiber has only the latter mechanism available. Since hydrophobic fibers have low surface tension as shown by high contact angles, water tends to form droplets on the fiber surface. Thus wetting does not occur and moisture absorption into the matt structure is negligible or extremely slow.

The total absorbent capacity of a structure is also dependent on the ability of the fiber in the matt structure to resist the driving forces developed by surface tension effects. The forces will attempt to collapse the matt structure reducing interstitial volume and hence total absorbent capacity.

The ability of a matt structure to resist wet collapse depends on the resiliency of the constituent fibers. One method of measuring resiliency is the ability of fibers or fiber structure to recover from deformation and its extent of recovery. If a fiber has poor recovery under wet conditions, the matt structure will become disheveled and in disarray.

The water-absorbent matts of the present invention wick rapidly and hold water and aqueous solutions both within and between the melt-blown fibrils. The resulting mat is resistant to laundering conditions such as high washing temperatures, mechanical abrasion during the wash cycle, and high concentrations of laundry bleach. The matt structure of the invention may incorporate other fibers such as polypropylene fiber.

The matt structures are useful for diapers, wiping cloths, athletic undergarments, toweling, bedding, medical gauzes, dressings, and bandages, and filters for removal of an aqueous phase from a largely nonaqueous suspension, and other applications which require a high rate of moisture uptake with a high liquid content, good resilience both wet and dry, strength, and durability.

EXAMPLE 1

Low Molecular Weight Polymer, 15 Percent Polyether

In a 100-gallon pilot plant reactor, 385 lb of caprolactam at 90° C. was mixed with 57.7 lb of Jeffamine ED2001. To this was added 1.72 lb of Irganox 1010, 8.82 lb of terephthalic acid, 10.7 g of 50 percent hypophosphorous acid, 13 lb of water and 15 g of Dow Corning's DC-36 antifoam. The mixture was heated to 255° C., and an autogenous pressure of 80 psig was generated. This pressure was vented over a period of three hours. A vacuum of 10 mm Hg absolute was then attained without severe foaming, within 15 minutes.

The molten mixture was stirred using a double spiral agitator until the electrical load of the agitator motor became constant, about 8 hours. Then polymer strands were extruded from the bottom of the reactor, and pelletized. The pellets were subjected to five one-hour extractions with water at 95° C. to remove unreacted caprolactam, and then dried for 16 hours at 100° C., under nitrogen.

The washed and dried polymer had a relative viscosity in formic acid (FAV) of 22 with 130 carboxyl equivalents and 10 amine equivalents per $10^6$ grams of polymer.

EXAMPLE 2

Polymer Containing 40 Percent Polyether

In a 100-gallon pilot plant reactor, 220 lb of caprolactam at 90° C. was mixed with 123 lb of Jeffamine ED2001. To this was added 840 g of Irganox 1010, 4,200 g of terephthalic acid, 7.9 g of 50 percent hypophosphorous acid, 12 lb of water and 18 g of Dow Corning's DC-36 antifoam. The mixture was heated to 255° C., and an autogenous pressure of 85 psig was generated. This pressure was vented over a period of three hours. A vacuum of 10 mm Hg absolute was then attained without severe foaming, within 15 minutes.

The molten mixture was stirred using a double spiral agitator for 6 hours at 255° C. Then polymer strands were extruded from the bottom of the reactor, and pelletized. The pellets were subjected to five one-hour extractions with water at 95° C. to remove unreacted caprolactam, and then dried for 16 hours at 100° C., under nitrogen.

The washed and dried polymer had a relative viscosity in formic acid (FAV) of 35 with 29 carboxyl equivalents and 15 amine equivalents per $10^6$ grams of polymer.

EXAMPLE 3

Polymers made from different polyamide/polyether compositions are made into similar matts, with the same thickness and weighing about 0.34 kg/m². They are washed in a conventional home clothes washer and then spun dried. The water holding capacity after spin-drying is a measure of the water holding capacity.

| | Block Copolyetheramide | | |
|---|---|---|---|
| Test No. | Polyamide Segment, % | Polyether Segment, % | Grams Liquid/ Grams of Matt |
| 1 | 100 | 0 | 0.27 |
| 2 | 90 | 10 | 0.32 |
| 3 | 85 | 15 | 0.35 |
| 4 | 80 | 20 | 0.36 |

EXAMPLE 4

To determine the wickability or rate of wetting of a structure, an eye-dropper which delivers a water drop of 0.05 cc is positioned directly above the surface of the fabric. One drop is placed on the fabric and 30 seconds later the wetted area is measured.

The results of this test on sample matts are as follows.

| | Block Copolyetheramide | | |
|---|---|---|---|
| Test No. | Polyamide Segment, % | Polyether Segment, % | Wetted Area, inches² |
| 1 | 100 | 0 | 0.25 |
| 2 | 90 | 10 | 0.90 |
| 3 | 85 | 15 | 0.97 |
| 4 | 80 | 20 | 0.95 |

EXAMPLE 5

The rate of water transport across the matt is measured by cutting the matt into 2.5 cm wide strips, 250 cm long. One end of the strip is put into a pool of distilled water at 20° C. The height of the water front is determined after 10 minutes.

| | Block Copolyetheramide | | |
|---|---|---|---|
| Test No. | Polyamide, % | Polyether, % | Liquid Height, cm |
| 1 | 100 | 0 | 2.5 |
| 2 | 90 | 10 | 9.6 |
| 3 | 85 | 15 | 11.0 |
| 4 | 80 | 20 | 11.6 |

EXAMPLE 6

Matt samples are exposed to 65 percent relative humidity (RH) at 20° C., and to 95 percent RH at 32° C. and the weight percent moisture regain determined.

| | Block Copolyetheramide | | | |
|---|---|---|---|---|
| | | | Regain, Wt % | |
| Test No. | Polyamide Segment, % | Polyether Segment, % | 65% RH at 20° C. | 95% RH at 32° C. |
| 1 | 100 | 0 | 4–5 | 8–9 |
| 2 | 90 | 10 | 4–5 | 11–12 |
| 3 | 85 | 15 | 5–6 | 12–13 |
| 4 | 80 | 20 | 5–6 | 14–15 |

EXAMPLE 7

The effect of extended exposure to hypochlorite bleach was simulated by adding 4 times the recommended amount of sodium hypochlorite bleach to a home clothes washer and then washing matt samples for 20 minutes at 60° C. The calculated sodium hypochlorite concentration is 0.086 percent. The results of tests on the treated matts are as follows.

| | Grab Break Strength, lb | Moisture Regain at 35° C. 90% RH | Wicking, Rise in 10 mins, cm |
|---|---|---|---|
| 100% Polyamide | | | |
| original | 70 | 7.3 | 2.8 |
| washed | 75 | 7.1 | 2.7 |
| 85% Polyamide, 15% Polyether | | | |
| original | 74 | 14.5 | 15.0 |
| washed | 69 | 15.5 | 13.5 |

Details of method of measuring Grab Break Strength is provided by ASTM D-1682.

EXAMPLE 8

Fibers were made from conventional nylon 6 and from hydrophilic nylon of this invention by a spinning method involving high melt attenuation in order to simulate the formation of melt-blown fibers. The tensile properties of these fibers were found to have about 60 percent elongation. The tensile recoveries from 10 percent elongation were measured under different conditions. They are tabulated below.

| | Tensile Recovery from 10% Strain | |
|---|---|---|
| Yarn Conditions | Conventional Nylon 6 100% Polyamide | 85% Polyamide 15% Polyether |
| 65% RH at 20° C., % | 81.3 | 86.3 |
| 10 min soaked in water at 20° C., % | 74.8 | 84.8 |
| 24 Hours over water at 100% RH, 20° C., % | 86.8 | 90.2 |

The greater elastic recovery of the copolymer demonstrates the good resilience of the copolymers when made into matts and exposed to humid conditions.

EXAMPLE 9

The spontaneous uptake of matts weighing about 0.34 kg/m² made from conventional nylon 6 (100 percent polyamide), and from a copolyetheramide (85 percent polyamide 15 percent polyether), are measured using the instrument described in B. Miller and I. Tyomkin, "An Extended Range Liquid Extrusion Method for Determining Pore Size Distributions", Textile Research Journal 56, 35–40 (1986). The liquid used is water with 0.1 percent Triton X-100, a polyethoxylated octylphenol from Rohm and Haas, Philadelphia, Pa. The opposing pressure head was 3 cm of water. The results of the tests are listed below. The maximum rate of water uptake, $(\Delta W/\Delta T)_{max}$ in mg/cm² second is listed in the first column. The second column lists the time taken by the matt to imbibe 50 percent of its equilibrium capacity, $t_{50}$, in seconds.

|  | $(\Delta W/\Delta T)_{max}$ | $t_{50}$ |
|---|---|---|
| Conventional Nylon 6 (100/0) | 0.18 | 290 |
| Copolyetheramide (85/15) | 1.00 | 50 |

EXAMPLE 10

The contact angles between liquid water and the fiber surface is measured by the Wilhelmy wetting force scanning technique, in the advancing mode. The results are listed below.

| Fiber | Contact Angle, Advancing, degrees |
|---|---|
| Conventional Nylon 6 (100% polyamide) | 69 |
| Copolyetheramide (85% polyamide, 15% polyether) | 54 |
| Polyethylene terephthalate | 80 |
| Polypropylene | 90 |

The greater the angle the less the tendency of the fiber to be wetted with water. The Wilhelmy method is described in *Physical Chemistry of Surfaces* by A. W. Adamson, Interscience 1967, p 27.

We claim:

1. A melt-blown water-absorbing matt of fibers comprising
a block copolyetheramide having a number average molecular weight of from about 10,000 to about 35,000 and having polymer segments of the following structure:
   (A) a polyether segment consisting predominantly of

where c is at least 1, (a+c) is at least 1 but less than 10 and b is at least 10 but less than 150;
   (B) a polyamide segment consisting of at least one of the following:

 (1)

 (2)

where $R_1$, $R_2$ and $R_3$ are each selected from the same or different alkylene or substituted alkylene moieties of from 4 to 11 carbons and difunctional aromatic moieties; wherein the concentration of segment A in the copolymer is between from about 10 to about 50 percent by weight of copolyether amide.

2. The matt of claim 1 wherein a phenolic antioxidant is used in the copolymer where the ratio of antioxidant to polyether segment is greater than 0.01 but less than 0.1 by weight.

3. The matt of claim 2 wherein said copolymer additionally contains a dicarboxylic acid.

4. The matt of claim 3 wherein said dicarboxylic acid is selected from the group consisting of adipic, azelaic, terephthalic, isophthalic, dodecanedioic, sebacic and naphthalene dibasic acid.

5. The matt of claim 4 wherein said dicarboxylic acid is terephthalic acid.

6. The matt of claim 3 wherein the antioxidant is tetrakis(methylene(3,5-di-t-butyl-4-hydroxy-hydrocinnamate))methane.

7. The matt of claim 3 further comprising polypropylene fiber.

* * * * *